United States Patent
Levin et al.

(10) Patent No.: US 9,591,981 B2
(45) Date of Patent: Mar. 14, 2017

(54) MULTI-CHANNEL ECG MEASUREMENT

(71) Applicant: BIOSENSE WEBSTER (ISRAEL), LTD., Yokneam (IL)

(72) Inventors: Michael Levin, Haifa (IL); Meir Bar-Tal, Haifa (IL)

(73) Assignee: Biosense Webster (Isreal) Ltd., Yokneam (IL)

( * ) Notice: Subject to any disclaimer, the term of this patent is extended or adjusted under 35 U.S.C. 154(b) by 815 days.

(21) Appl. No.: 13/693,099

(22) Filed: Dec. 4, 2012

(65) Prior Publication Data

US 2014/0155723 A1 Jun. 5, 2014

(51) Int. Cl.
| | |
|---|---|
| *A61B 5/0408* | (2006.01) |
| *A61B 5/00* | (2006.01) |
| *A61B 5/04* | (2006.01) |
| *A61B 5/0402* | (2006.01) |

(52) U.S. Cl.
CPC ...... *A61B 5/04085* (2013.01); *A61B 5/04001* (2013.01); *A61B 5/0402* (2013.01); *A61B 5/04012* (2013.01); *A61B 5/04028* (2013.01); *A61B 5/7203* (2013.01); *A61B 5/7228* (2013.01)

(58) Field of Classification Search
CPC . A61B 5/7203; A61B 5/7228; A61B 5/04001; A61B 5/04085; A61B 5/0402; A61B 5/04028; A61B 5/04012
USPC ....................................... 600/509
See application file for complete search history.

(56) References Cited

U.S. PATENT DOCUMENTS

| | | |
|---|---|---|
| 3,868,948 A | 3/1975 | Graetz |
| 4,887,609 A | 12/1989 | Cole, Jr. |
| 5,188,117 A | 2/1993 | Steinhaus et al. |
| 5,349,352 A | 9/1994 | Saleh |
| 5,392,784 A | 2/1995 | Gudaitis |
| 5,406,955 A | 4/1995 | Bledsoe |
| 6,216,031 B1 | 4/2001 | Findeis et al. |
| 6,532,379 B2 | 3/2003 | Stratbucker |
| 6,807,443 B2 | 10/2004 | Keren |
| 7,277,754 B2 * | 10/2007 | McCabe .............. A61N 1/3704 128/923 |
| 7,970,460 B2 | 6/2011 | Li et al. |

(Continued)

FOREIGN PATENT DOCUMENTS

| | | |
|---|---|---|
| WO | WO 2007/058950 A2 | 5/2007 |
| WO | WO 2010/103542 A2 | 9/2010 |

OTHER PUBLICATIONS

EP Search Report—EP 13 19 5423 Dated Feb. 18, 2014.

(Continued)

*Primary Examiner* — Mark W Bockelman
(74) *Attorney, Agent, or Firm* — Louis J. Capezzuto (57) ABSTRACT

A method for acquiring electrical signals from a living subject, including injecting, via an injection electrode attached to the subject, a known calibration signal to the subject and measuring respective levels of output signals generated at input electrodes attached to the subject in response to the calibration signal. The method further includes deriving respective weighting factors for the input electrodes in response to the respective levels, and applying the respective weighting factors to physiological signals acquired by the input electrodes, so as to generate respective corrected physiological signals.

9 Claims, 3 Drawing Sheets

(56) References Cited

U.S. PATENT DOCUMENTS 8,043,226 B2 10/2011 Kim et al.
2011/0066052 A1 3/2011 Mascaranhas

OTHER PUBLICATIONS

Levkov, C. et al. *Removal of Power-Line Interference From the ECG: A Review of the Subtraction Procedure*. Biomedical Engineering Online 2005, 4:50.
Hamilton, P.S. *A Comparison of Adaptive and Nonadaptive Filters for Reduction PF Power Line Interference in the ECG*. IEEE Transactions on Biomedical Engineering, 43(1), pp. 105-109, 1996.
Kumaravel et al. *Integrating the ECG Power-Line Interference Removal Methods With Rule-Nased System*. Biomed Sci Instrum., 31, pp. 115-120, 1995.
Limacher, R. *Removal of Power Line Interference From the ECG Signal by an Adaptive Digital Filter*. ETC 96, Proc. of Europ. Telemetry Conf., Garmisch-Part., May 21-21, 1996.
Yu, CH. et al. *The Realization of Tracking Power-Line Interference Adaptive Coherent Model Based on Part FFT*, Journal of Physics: Conference Series 13, pp. 274-279, 2005.

\* cited by examiner

MULTI-CHANNEL ECG MEASUREMENT

FIELD OF THE INVENTION

The present invention relates generally to improvement in the accuracy of signal measurement, and reduction of interference in signal measurement, and specifically to reduction of interference in electrocardiograph (ECG) measurements.

BACKGROUND OF THE INVENTION

Electrocardiograph (ECG) signals include signals that are measured from leads external to the heart, typically that are attached to the body surface (BS), as well as those from intra-cardiac (IC) electrodes contacting the heart. The signals are inherently relatively low level signals and have relatively high impedance sources. Because of this and other environmental factors, in medical procedures such as mapping the electrical activity of the heart, the measurements are typically relatively noisy. A system to increase the accuracy of the measurements, and to reduce the effect of the noise on the measurements would be beneficial.

SUMMARY OF THE INVENTION

An embodiment of the present invention provides a method for acquiring electrical signals from a living subject, including:

injecting, via an injection electrode attached to the subject, a known calibration signal to the subject;

measuring respective levels of output signals generated at input electrodes attached to the subject in response to the calibration signal;

deriving respective weighting factors for the input electrodes in response to the respective levels; and applying the respective weighting factors to physiological signals acquired by the input electrodes, so as to generate respective corrected physiological signals.

Typically the physiological signals include signals generated from electrophysiological processes occurring in the subject.

In a disclosed embodiment the physiological signals include signals generated externally to the subject, and which are coupled into the subject.

In a further disclosed embodiment the known calibration signal has a preset frequency, and measuring respective levels of the output signals includes measuring the respective levels at the preset frequency.

In a yet further disclosed embodiment the respective levels include respective amplitude levels generated at the input electrodes, and the respective weighting factors are derived in response to inverse values of the respective amplitude levels. Alternatively or additionally, the respective levels may include respective phase levels generated at the input electrodes, and the respective weighting factors may be derived in response to negative values of the respective phase levels.

In an alternative embodiment the physiological signals include bipolar signals, and the corrected physiological signals include corrected bipolar signals. Alternatively or additionally, the physiological signals include unipolar signals, and the corrected physiological signals include corrected unipolar signals.

In a further alternative embodiment the input electrodes include three electrodes respectively attached to a right arm (RA), a left arm (LA), and a left leg (LL) of the subject, and applying the respective weighting factors to the three physiological signals acquired by the three electrodes includes averaging the three corrected physiological signals generated from the three electrodes to provide a reference signal.

There is further provided, according to an embodiment of the present invention, apparatus for acquiring electrical signals from a living subject, including:

an injection electrode attached to the subject;
input electrodes attached to the subject; and
a processor, which is configured to:
inject a known calibration signal to the subject via the injection electrode, measure respective levels of output signals generated at the input electrodes in response to the calibration signal, derive respective weighting factors for the input electrodes in response to the respective levels, and apply the respective weighting factors to physiological signals acquired by the input electrodes, so as to generate respective corrected physiological signals.

The present disclosure will be more fully understood from the following detailed description of the embodiments thereof, taken together with the drawings, in which:

DETAILED DESCRIPTION OF EMBODIMENTS

Overview

An embodiment of the present invention provides a system for measuring and compensating channel inaccuracy caused by pick up from sources and channel component variations. The measurement and compensation is typically necessary because the subject may be in an environment where she/he picks up extraneous electrical signals, such as power line signals. The physiological signals may comprise any electrical signals generated by electrical activity of the subject, such as electromyograph (EMG), electroencephalograph (EEG), or electrocardiograph (ECG) signals. For simplicity, the following description assumes the electrical signals are ECG signals.

In order to provide the correction, a known calibration signal is injected into the subject via an injection reference electrode attached to the subject. The calibration signal typically comprises a spectrum of frequencies. Input electrodes are also attached to, or connected to, the subject. The electrodes, in the case of ECG, receive body surface (BS) ECG signals from electrodes attached to the skin of the subject, and/or intra-cardiac (IC) ECG signals from electrodes that are typically on one or more catheters in the subject's heart.

A processor measures levels of signals that are simultaneously received by the input electrodes in response to the calibration signal, and for each input electrode the processor compares the measured signals to the calibration signal. The comparison may be performed for the amplitudes and the phases of the signals over the spectrum of frequencies of the injected signal. From the comparison, the processor derives respective weighting factors for each of the input electrodes. The weighting factors are a measure of the effect of the injected signal at the respective input electrodes.

For each of the input electrodes the processor applies the weighting factors to physiological signals acquired by the electrodes, in the example described here ECG signals, to obtain corrected physiological signals.

The corrected signals may be in unipolar or bipolar form. Signals, as corrected by embodiments of the present invention, have a significant improvement in measured accuracy compared to the uncorrected signals, as well as in comparison with prior art systems. In addition, the corrected signals, as generated by embodiments of the present invention substantially reduce, or even eliminate, the effects of extraneous signals such as power line signals that may interfere with signals generated by the subject.

The system described herein may be used for real-time monitoring of parameters associated with acquisition of physiological signals, such as parameters measuring differences between the channels and circuits associated with the electrodes acquiring the signals. The differences typically include deviations in operating parameters of components associated with the channels, as well changes in electrode-tissue contact impedances. An additional advantage provided by the system is excellent common-mode rejection of externally induced signals, such as those from power lines.

In one embodiment of the present invention, an equivalent of a Wilson central terminal (WCT) is generated by acquiring respective physiological signals from input electrodes attached to the right arm, the left arm, and the left leg of the subject. The calibration signal is injected into the right leg of the subject. The three corrected signals from the input electrodes are averaged to produce a reference ground level. The reference signal for other channels. This reference signal may be used as the reference of unipolar signals, and provides a more exact reference than prior art grounds because of the corrections applied to the three input electrode physiological signals.

System Description

Figure 1:
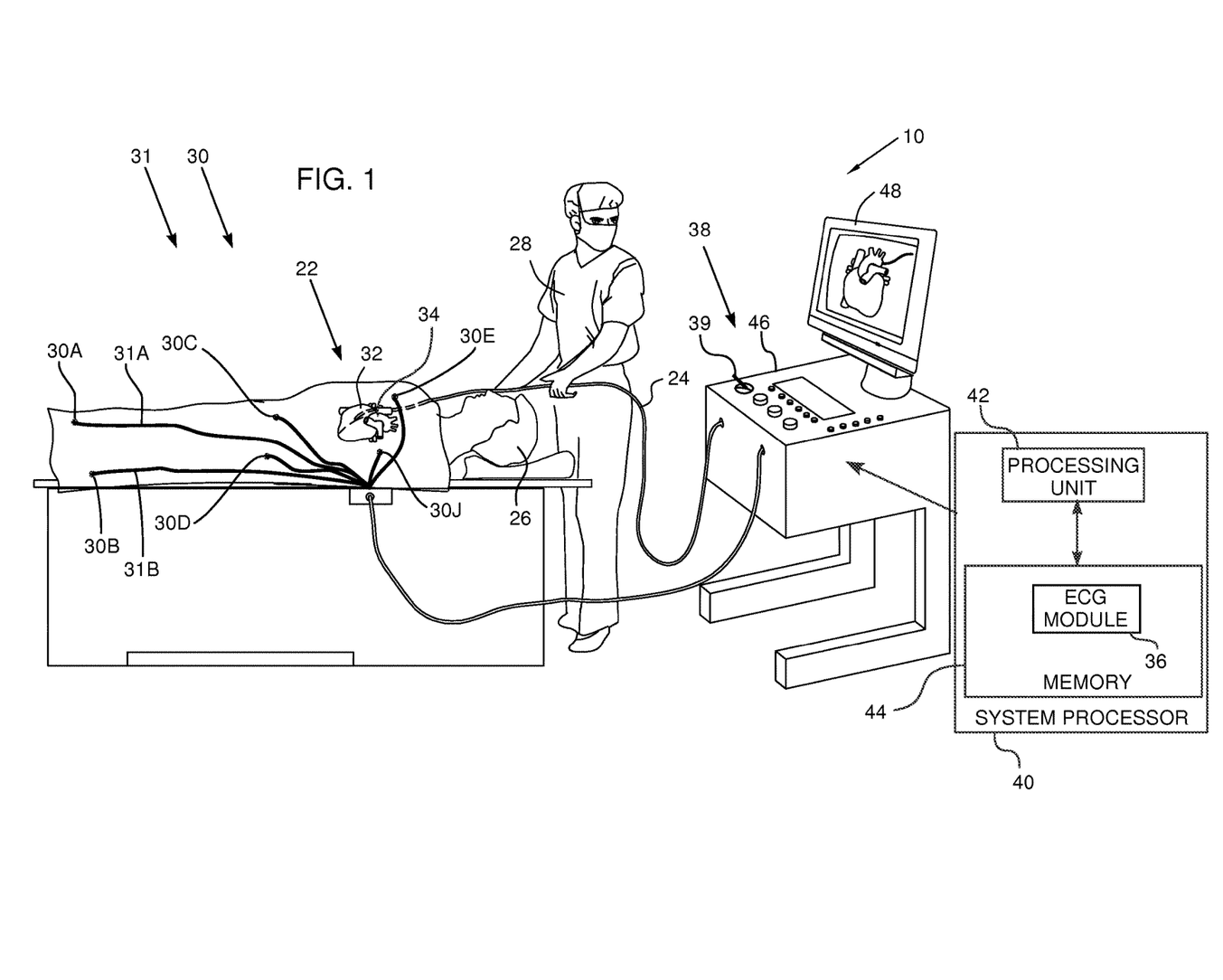
FIG. 1 is a schematic illustration of a multi-channel electrocardiograph (ECG) signal measurement system, according to an embodiment of the present invention.

Reference is now made to FIG. 1, which is a schematic illustration of a multi-channel electrocardiograph (ECG) signal measurement system 10, according to an embodiment of the present invention.

For simplicity and clarity, the following description, except where otherwise stated, assumes an investigative procedure wherein system 10 senses body surface (BS) electrical signals from a heart 34 of a subject 26. However, embodiments of the present invention may be applied to both BS and intra-cardiac (IC) electrical signals. IC signals are typically acquired using a probe 24 which has a distal end 32 having one or more IC electrodes 22.

In order to sense BS electrical signals, electrodes 30A, 30B, 30C, . . . are attached to the skin of subject 26 by respective leads 31A, 31B, 31C, . . . . In the present disclosure electrodes 30A, 30B, 30C, . . . are collectively termed electrodes 30, and leads 31A, 31B, 31C, . . . are collectively termed leads 31. In a typical ECG procedure where only BS electrical signals are measured, there are ten electrodes 30 attached to the skin of subject 26 in standard positions: right arm, left arm, right leg, left leg, as well as six electrodes in the region of heart 34. In FIG. 1 four electrodes 30A, 30B, 30C, and 30D, are illustrated, and are assumed to be respectively attached to the right leg, left leg, right arm, and the left arm of subject 26. For clarity, only two electrodes 30E and 30J of the six electrodes attached in the region of heart 34, for the typical ECG procedure referred to above, are shown in FIG. 1.

However, there may be more than ten, or fewer than ten, electrodes 30 in some ECG procedures, and there is no restriction on the number of electrodes 30 for embodiments of the present invention. Similarly, in the case of IC electrical signals, there is no restriction on the number of IC electrodes 22 which may be used in system 10. It will be understood that each electrode (of electrodes 30 and electrodes 22) defines a respective channel of system 10.

Typically, probe 24 comprises a catheter which is inserted into the body of a subject 26 during a medical procedure performed by a user 28 of system 10. In the description herein user 28 is assumed, by way of example, to be a medical professional.

System 10 may be controlled by a system processor 40, comprising a processing unit 42 communicating with a memory 44. Processor 40 is typically mounted in a console 46, which comprises operating controls 38, typically including a pointing device 39 such as a mouse or trackball, that professional 28 uses to interact with the processor. The processor uses software, including an ECG module 36, stored in memory 44, to operate system 10. Results of the operations performed by processor 40 are presented to the professional on a display 48, which typically presents a graphic user interface to the user, a visual representation of the ECG signals sensed by electrodes 22 and/or electrodes 30, and/or an image or map of heart 34 while it is being investigated. The software may be downloaded to processor 40 in electronic form, over a network, for example, or it may, alternatively or additionally, be provided and/or stored on non-transitory tangible media, such as magnetic, optical, or electronic memory.

ECG module 36 is coupled to receive electrical signals from electrodes 22 and electrodes 30. The module is configured to analyze the signals and may present the results of the analysis in a standard ECG format, typically a graphical representation moving with time, on display 48. The structure and operation of module 36 is described in more detail below with respect to FIG. 2 and FIG. 3.

Figure 2:
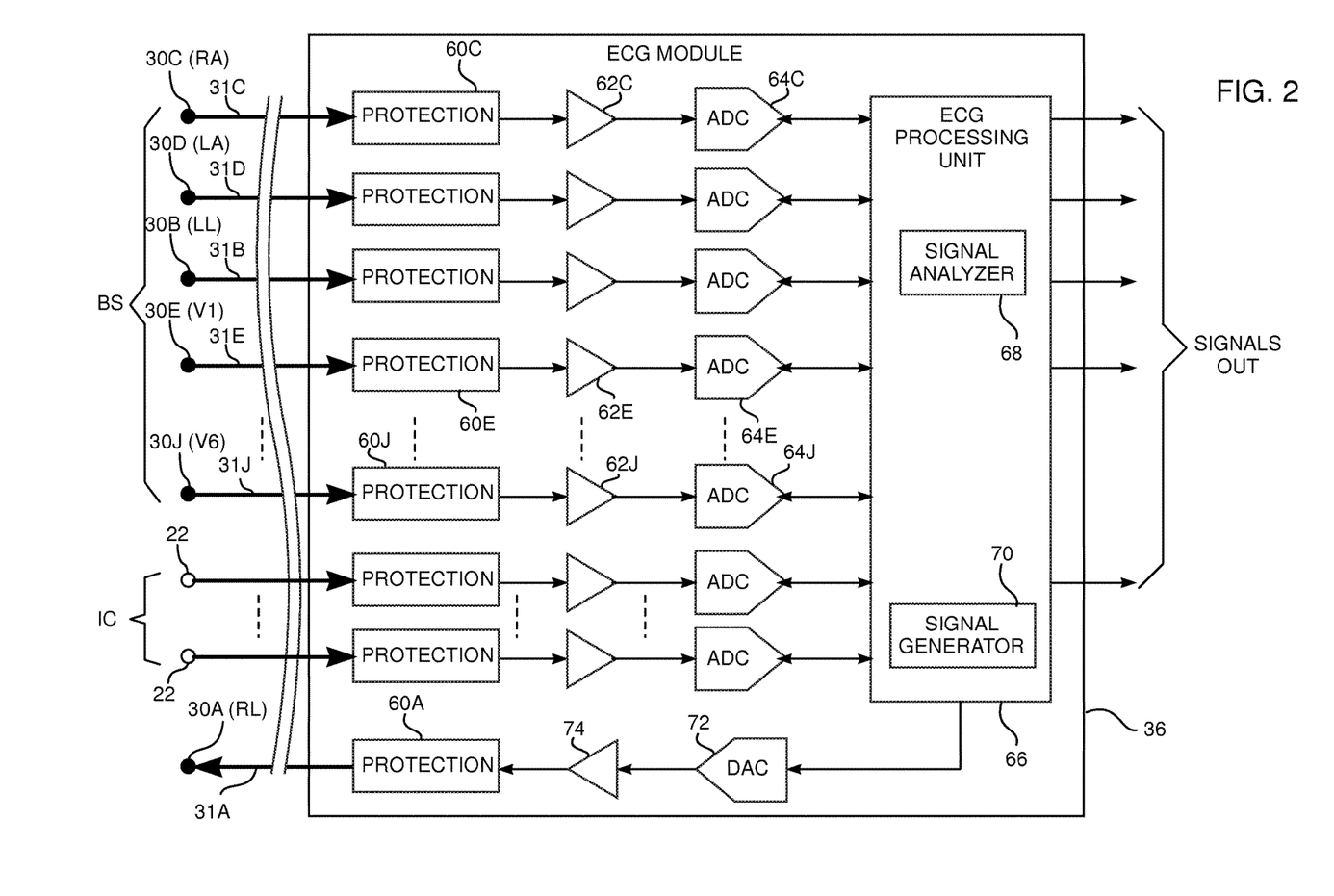
FIG. 2 is a schematic block diagram of an ECG module, according to an embodiment of the present invention.

FIG. 2 is a schematic block diagram of ECG module 36, according to an embodiment of the present invention. In FIG. 2, the identifiers for electrodes 30A, 30B, 30C, and 30D have been appended with identifiers of the respective limb, right leg (RL), left leg (LL), right arm (RA), and left arm (LA) to which the electrodes are attached. In the disclosure electrodes 30E, 30F, 30G, 30H, 30I, and 30J may also respectively be identified by voltage identifiers V1, V2, V3, V4, V5, and V6. FIG. 2 illustrates electrodes 30E and 30J having appended voltage identifiers V1, V6. For clarity, in the figure BS electrodes 30 are shown as solid circles, whereas IC electrodes 22 are shown as open circles.

Except for the circuitry within module 36 that is connected to electrode 30A, on the right leg of subject 26, the circuitry within module 36 that is connected to each of the other electrodes 30, and to electrodes 22, is substantially similar. The following description applies to the circuitry connected to BS electrode 30E, and applies, with an appropriate change of suffix letter, to the circuitry connected to all the other electrodes 30 except for electrode 30A. The description also applies to the circuitry connected to the one or more IC electrodes 22.

Electrode 30E is connected via a lead 31E to a protection device 60E, typically a voltage suppressor. Device 60E insulates components of module 36 from unwanted currents or voltages that may be generated in subject 26, such as those generated from defibrillation or ablation procedures.

The signals present at electrode 30E are typically generated from electrophysiological processes occurring in subject 26, such as the ECG signals associated with the beating of heart 34. The signals present at electrode 30E may also include signals that have been generated externally to subject 26, which are picked up by, or coupled into, the subject, and which are transferred to the electrode via the subject. Such latter signals include electrical signals generated by power line pickup of subject 26.

Signals at electrode 30E include physiological signals as well as a signal generated in response to a signal injected into subject 26, described in more detail below. The signals at electrode 30E are conveyed to device 60E. After traversing device 60E, the output signals are amplified in a low-noise high-impedance amplifier 62E, and the amplified output signals are then digitized in an analog to digital converter (ADC) 64E. In one embodiment ADC 64E comprises an ADS1271 produced by Texas Instruments, Dallas, Tex. The digitized data from electrode 30E, and the digitized data from all the other electrodes apart from electrode 30A, are transferred to an ECG processing unit 66 for analysis in a signal analyzer 68 in the unit.

Electrode 30A is connected to a protection device 60A. However, rather than signals originating in subject 26 being transferred via the electrode to unit 66, the electrode is configured to inject signals into the subject. The signal injection occurs at the region of subject 26 where electrode 30A is attached, i.e., at the right leg of the subject.

The injected signals are generated by a digital signal generator 70, which supplies digitized values to a digital to analog converter (DAC) 72. DAC 72 converts the digital data from generator 70 to an analog signal, and the analog signal is transferred via a buffer amplifier 74 to electrode 30A.

Figure 3:
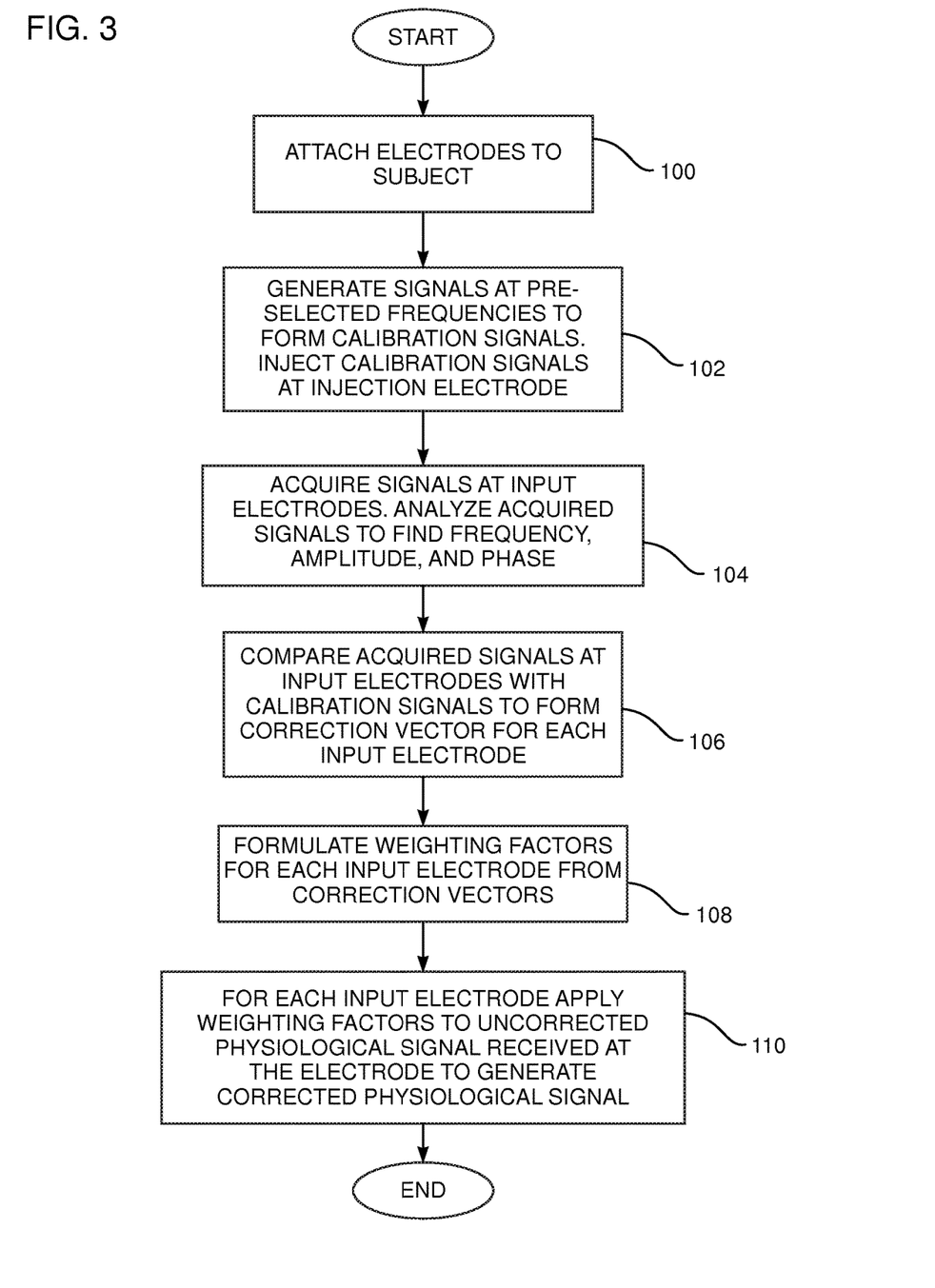
FIG. 3 is a flowchart of steps performed by a processor in operation of the multi-channel ECG signal measurement system, according to an embodiment of the present invention.

FIG. 3 is a flowchart of steps performed by processor 40 in operation of system 10, according to an embodiment of the present invention. The description of the flowchart assumes that the typical system of ten electrodes 30 is attached to the skin of subject 26. Those having ordinary skill in the art will be able to adapt the description for the case where other electrodes operate within subject 26, such as having at least some IC electrodes 22 positioned in heart 34 to generate IC signals, and/or for other numbers of electrodes 30. The flowchart description also assumes that ECG measurements of subject 26 are to be made while the steps of the flowchart are performed, i.e., simultaneously with the performance of the flowchart steps.

In the description of the flowchart, electrode 30A may be referred to as the reference signal injection electrode, the reference electrode, or the injection electrode. In addition, electrodes 30B-30J may be referred to as the signal receiving electrodes, or as the input electrodes.

In an initial step 100 ten electrodes 30 are attached to the skin of subject 26, the electrodes being positioned substantially as described above with reference to FIG. 1. The electrodes are connected to ECG module 36, via console 46, as shown in FIG. 2.

In a signal generation step 102, signal generator 70 generates a digital signal having n pre-selected frequencies $f_1, f_2, \ldots f_n$ with respectively n pre-selected phases $\phi_1, \phi_2, \ldots \phi_n$, where n is an integer equal to 1 or more. The signal is input to DAC 72, and the analog signal from DAC 72 is amplified by amplifier 74. For each frequency $f_1, f_2, \ldots f_n$ a respective amplification factor $A_1, A_2, \ldots A_n$ of amplifier 74 is set, typically by processing unit 66, so that the level of the signal output by the amplifier is a known, pre-selected, value for all n frequencies.

Frequencies $f_1, f_2, \ldots f_n$ are typically selected to be in a range comprising expected ECG signal frequencies, and expected power line interference frequencies. The latter are typically approximately 50 Hz or 60 Hz. The former are typically in the range of approximately 1 Hz to approximately 1000 Hz. However, there is no requirement that the frequencies of the signal generated by generator 70 are within the values listed above, and frequencies $f_1, f_2, \ldots f_n$ may be outside these values.

An expression for a calibration signal input to electrode 30A is given by:

$$S_{cal}=S_i(V_i) \quad (1)$$

where $S_i$ is an input function, typically a sinusoidal function, of a vector $V_i$, vector $V_i$ is a 3n-dimensional input vector having elements defining the amplitude, frequency, and phase of the n different signals, i.e., $$V_i=(A_1, A_2, \ldots A_n, f_1, f_2, \ldots f_n, \phi_1, \phi_2, \ldots \phi_n),$$

and $S_{cal}$ is the calibration signal injected to electrode 30A; the levels of calibration signal $S_{cal}$ are assumed to be measured relative to an isolated ground of ECG module 36.

The n different signals of the injected calibration signal $S_{cal}$, may be applied sequentially. Alternatively, at least some of the n different signals of $S_{cal}$ may be applied simultaneously.

In some embodiments, calibration signal $S_{cal}$ is modulated, typically by a suitable analog or digital modulation technique, in order to facilitate detection of the signals resulting from the injected calibration signal. Such modulation of the calibration signal enables processor 40 to distinguish signals resulting from the injected signal, even if such signals have frequencies similar to physiological signals (such as ECG or induced power line signals) generated in, or transferred via, subject 26 and defined above. The detection of the resulting signals is described below.

Injected calibration signal $S_{cal}$ is conveyed to the injection electrode, and the injected signal simultaneously produces corresponding output signals at the input electrodes attached to subject 26. These corresponding output signals are superimposed on physiological signals and picked-up noise on the input electrodes that are generated by other sources. Such other sources include the ECG signals generated by the beating of heart 34, as well as external sources such as radiative, inductive, or capacitive coupling from power line instruments in the vicinity of subject 26.

In a signal acquisition step 104, signals from the input electrodes are acquired by signal analyzer 68. Using the known frequencies $f_1, f_2, \ldots f_n$ of calibration signal $S_{cal}$, together with any modulation parameters that may have been applied to the calibration signal, the signal analyzer uses phase sensitive detection to determine values of the effective signal induced at the electrode by the calibration signal.

An expression for the induced effective signal that is generated at an input electrode $E_a$ is given by:

$$S_{eff}(E_a)=S_o(V_{ao}) \quad (2)$$

where $E_a$ is an identifier of the input electrode, $S_o$ is an output function of an output vector $V_{ao}$, and vector $V_{ao}$ is a 3n-dimensional output vector having elements defining the amplitude, frequency, and phase of the n different signals at the input electrode, i.e., $$V_o \equiv (A_{ao1}, A_{ao2}, \ldots A_{aon}, f_1, f_2, \ldots f_n, \varphi_{ao1}, \varphi_{ao2}, \ldots \varphi_{aon}),$$

and $S_{eff}(E_a)$ is the effective output signal formed at input electrode $E_a$ by the injected calibration signal $S_{cal}$.

Output function $S_o$ is typically similar to input function $S_i$, so that if the latter is sinusoidal $S_o$ is also sinusoidal.

It will be understood that while vectors $V_i$ and $V_{ao}$ typically have differing values of amplitude and phase elements, they have common frequency elements $f_1, f_2, \ldots f_n$.

In the following description, "a" is assumed to be an integer between 1 and 9, corresponding to the nine BS input electrodes attached to subject 26. Alternatively, where appropriate, "a" may be one of RA, LA, LL, V1, ... V6.

Steps 102 and 104 are typically implemented during substantially the whole course of a procedure being performed on subject 26. In some embodiments the steps are implemented intermittently, so that there are some times during a procedure when there is no injection of a calibration signal into the subject. In the case of an intermittent implementation, results (described below) obtained during the step implementation may be used when the steps are not implemented, i.e., when there is no calibration signal injection. Also, in the case of intermittent implementation, the calibration signal is injected into subject 26 over a period of time sufficient to attain values of $S_{eff}(E_a)$ for each input electrode $E_1, \ldots E_9$ that have acceptable signal to noise values.

In a collation step 106, the different output values of the amplitudes and phases of $V_{ao}$, for the different frequencies $f_1, \ldots f_n$, are compared with the respective input levels of $V_i$. The comparison is performed for each input electrode $E_a$. For each input electrode, the comparison typically comprises forming a ratio of the output to the input amplitude levels and a difference of the phase levels. From the comparison, a set of 2n dimensional correction vectors $(C)E_1, \ldots (C)E_a, \ldots (C)E_9$, for each of the electrodes $E_1, \ldots E_a, \ldots E_9$ is formed.

An equation for correction vector $(C)E_a$ is:

$$(C)E_a \equiv \left( \frac{A_{ao1}}{A_1}, \ldots \frac{A_{aon}}{A_n}, (\varphi_{ao1} - \varphi_1), \ldots (\varphi_{aon} - \varphi_n) \right) \quad (3)$$

2n dimensional vector $(C)E_a$ comprises a set of n amplitude elements $$\frac{A_{ao1}}{A_1}, \ldots$$

and a set of n phase elements $(\varphi_{ao1} - \varphi_1), \ldots$ The amplitude elements are also referred to generically as $\{A_{ae}\}$, and the phase elements are also referred to generically as $\{\varphi_{ae}\}$. Each vector $(C)E_a$ formed in step 106 represents the signal resulting at the respective input electrode $E_a$ in response to the calibration signal injected at the injection electrode 30A.

Inspection of equation (3) demonstrates that the elements of correction vector $(C) E_a$ provide a numerical measure of the comparative effects of a signal injected into subject 26.

Typically, the differences in response at the different input electrodes, illustrated by the differing values of the elements of the correction vectors, are caused by multiple factors. Such factors include electrode contact impedance variations, differences in characteristics of electronic components, temperature differences of the electrodes and/or components connected to the electrodes, as well as the power transfer from the injection electrode to the input electrodes being non-uniform. As described below, embodiments of the present invention use the measured values of elements of the correction vectors to compensate for the difference in response of the input electrodes.

As a numerical example of equation (3), calibration signal $S_{cal}$, that is injected into the injection electrode, may be formed of a 10 mV signal at a frequency of 30 Hz, and a 20 mV signal at a frequency of 100 Hz, both signals having phases of 0. In this case $(V_i) \equiv (10, 20, 30, 100, 0, 0)$.

At electrode $E_1$ measured values at 30 Hz may be $A_{1o1}=4$ mV, $\Phi_{1o1}=+30°$ and at 100 Hz may be $A_{1o2}=12$ mV, $\varphi_{1o1}=-50°$; at electrode $E_6$ the measured values at 30 Hz may be $A_{6o1}=7$ mV, $\varphi_{6o1}=+20°$ and at 100 Hz may be $A_{6o2}=16$ mV, $\varphi_{6o2}=+0°$.

In this example, $(C)E_1 \equiv (0.4, 0.6, +30°, -50°)$, and $(C)E_6 \equiv (0.7, 0.8, +20°, +0°)$.

The elements of the correction vectors provide a numerical measure of how the injected signal affects each of the electrodes $E_1, E_2, \ldots E_9$. In addition, comparison between respective elements of the correction vectors provides a numerical measure of the relative effect on the electrodes of the injected signal. Thus, from the examples above, at the frequency of 30 Hz 40% of the injected signal appears at electrode $E_1$, whereas 70% appears at electrode $E_6$. Consequently, electrode $E_6$ responds to the injected signal by a factor of 0.7/0.4, =1.75, compared to electrode $E_1$.

In a weighting derivation step 108, processor 40 uses the elements of correction vectors $C(E_a)$ to formulate weighting factors to be applied to signals from each of the input electrodes. Application of the weighting factors to the signals counteracts the component of the physiological signals that is generated externally to subject 26. Such externally generated components are described above, and embodiments of the present invention simulate an external component by injection of the calibration signal into subject 26 from the injection electrode.

The weighting factors are typically formulated to have an "opposite" effect to that shown by the elements of the correction vectors.

Considering the amplitude elements of the correction vectors, corresponding amplitude weighting factors may be formulated as inverse values to those of the amplitude elements. In an embodiment of the present invention, an equation for an amplitude weighting factor $A_{aw}$ for electrode $E_a$ is:

$$A_{aw} = \frac{k_1}{A_{ae}} \quad (4)$$

where $A_{ae}$ is a generic amplitude element of correction vector $(C)E_a$ of electrode $E_a$, and $k_1$ is a constant.

Considering the phase elements of the correction vectors, corresponding phase weighting factors may be formulated as negatives of the values of the phase elements. In an embodiment of the present invention, an equation for a phase weighting factor $\varphi_{aw}$ for electrode $E_a$ is:

$$\varphi_{aw} = k_2 - \varphi_{ae} \quad (5)$$

where $\varphi_{ae}$ is a generic phase element of correction vector $(C)E_a$ of electrode $E_a$, and $k_2$ is a constant.

The description above illustrates the formulation of weighting factors for the discrete frequencies $f_1, \ldots f_n$. Processor 40 typically formulates sets of weighting factors for other frequencies, or for frequency bands, typically by interpolation or extrapolation.

Referring back to the numerical example of $(C)E_1$ and $(C)E_6$, at 30 Hz the amplitude elements are respectively 0.4 and 0.6. Using equation (4) and arbitrarily setting $k_1=1$, an amplitude weighting factor (at 30 Hz) for electrode $E_1$ is 2.5 and 1.2 for electrode $E_6$. However, any other convenient amplitude weighting factors may be used, based on equation (4). Using equation (5) and arbitrarily setting $k_2=0$, a phase weighting factor (at 30 Hz) for electrode $E_1$ is $-30°$ and $-20°$ for electrode $E_6$.

In a weighting factor application step 110, processor 40 applies the weighting factors determined in step 108 to the physiological signals received at the input electrodes, so as to generate corrected physiological signals.

Typically, processor 40 decomposes the physiological signal acquired into frequency components, which may comprise discrete frequencies or frequency bands, using Fourier analysis.

For each frequency component there is an uncorrected amplitude and an uncorrected phase. The uncorrected amplitude is multiplied by the appropriate amplitude weighting factor from step 108 to form a corrected amplitude. Similarly, the phase weighting factor from step 108 is added to the uncorrected phase to form a corrected phase. The corrected amplitude and corrected phase form a corrected frequency component.

The processor then recombines the corrected frequency components to form a corrected physiological signal. The process of decomposition, correction, and recombination of all the frequency components is applied separately to the physiological signal of each input electrode.

Application step 110 may be applied to signals that are bipolar or unipolar. For bipolar signals, the physiological signals from each of the two input electrodes generating the bipolar signal are separately corrected, and a difference between the two corrected signals is used as the corrected bipolar signal. An alternative method for producing corrected bipolar signals is described below.

It will be understood that application of the flowchart described above may be used for real-time monitoring of parameters associated with acquisition of physiological signals from a subject. Such parameters may indicate the condition of the circuits associated with the electrodes acquiring the signals, as well changes in electrode-skin contact impedances.

In some embodiments a unipolar signal may be measured relative to a group of input electrodes. Such a unipolar signal may use an equivalent of Wilson's central terminal (WCT). In prior art systems WCT may typically be formed by connecting RA, LA, and LL electrodes, i.e., electrodes 30B, 30C, and 30D via a resistive network, and a central connection point is used as a reference ground.

In contrast, embodiments of the present invention generate a WCT equivalent by acquiring respective physiological signals from the RA, LA, and LL electrodes. Each signal is corrected as described above using a process of decomposition, correction, then recombination, and the three corrected signals are averaged to provide a reference level that is used for forming the unipolar signal from a given input electrode (other than the RA, LA, and LL electrodes). Such a reference provides a better reference than prior art Wilson central terminals, since the corrections applied to the individual physiological signals of the RA, LA, and LL electrodes generate a more accurate reference.

The real-time capability of system 10, referred to above, allows dynamic adjustment of the WCT equivalent reference signal, permitting optimal common-mode rejection of external signals, such as power line pickup signals.

In some embodiments, a bipolar signal is formed by measuring two unipolar signals using the WCT equivalent described above. The bipolar signal is then formed by finding the difference between the two unipolar signals.

The above description has assumed that the calibration signal injected into subject 26 is injected into the right leg of the subject. However, it will be appreciated that this point of injection is selected by way of example, and embodiments of the present invention may use any other convenient location point on the subject as an injection point.

The above description has also generally referred to correction of ECG signals. However, it will be understood that embodiments of the present invention apply to correction of substantially any electrical signals generated by electrical activity of a living subject.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus for acquiring electrical signals from a living subject, comprising:
   an injection electrode adapted to be attached to a surface of a body of the subject;
   input electrodes adapted to be attached to a surface of a body of the subject; and
   a processor, which is configured to:
   inject a known calibration signal to the subject via the injection electrode,
   acquire the known calibration signal at the input electrodes, the input electrodes being adapted to generate output signals in response to the calibration signals,
   measure respective levels of output signals generated at the input electrodes in response to the calibration signal,
   derive respective weighting factors for each input electrode in response to the respective levels using a correction vector comprising a numerical measure of the known calibration signal acquired by each input electrode, and
   apply the respective weighting factors to physiological signals acquired by the input electrodes, so as to generate respective corrected physiological signals.

2. The apparatus according to claim 1, wherein the input electrodes acquire physiological signals comprising ECG signals.

3. The apparatus according to claim 1, wherein the input electrodes acquire physiological signals comprising induced power line signals generated externally to the subject.

4. The apparatus according to claim 1, wherein the known calibration signal has a preset frequency, and wherein measuring respective levels of the output signals comprises measuring the respective levels at the preset frequency.

5. The apparatus according to claim 1, wherein the respective levels comprise respective amplitude levels generated at the input electrodes, and wherein the respective weighting factors are derived in response to inverse values of the respective amplitude levels.

6. The apparatus according to claim 1, wherein the respective levels comprise respective phase levels generated at the input electrodes, and wherein the respective weighting factors are derived in response to negative values of the respective phase levels.

7. The apparatus according to claim 1, wherein the physiological signals comprise bipolar signals, and wherein the corrected physiological signals comprise corrected bipolar signals.

8. The apparatus according to claim 1, wherein the physiological signals comprise unipolar signals, and wherein the corrected physiological signals comprise corrected unipolar signals.

9. The apparatus according to claim 1, wherein the input electrodes comprise three electrodes respectively attached to a right arm (RA), a left arm (LA), and a left leg (LL) of the subject, and wherein applying the respective weighting factors to the three physiological signals acquired by the three electrodes comprises averaging the three corrected physiological signals generated from the three electrodes to provide a reference signal.

* * * * *